(12) United States Patent
Coddeville

(10) Patent No.: US 12,370,298 B2
(45) Date of Patent: Jul. 29, 2025

(54) FILTRATION UNIT FOR THE LEUCOCYTAPHERESIS OF THE BLOOD, COMPRISING A RELIEF-PERFORATED NONWOVEN

(71) Applicant: MACO PHARMA, Mouvaux (FR)

(72) Inventor: Maxime Coddeville, Lille (FR)

(73) Assignee: MACO PHARMA, Mouvaux (FR)

(*) Notice: Subject to any disclaimer, the term of this patent is extended or adjusted under 35 U.S.C. 154(b) by 693 days.

(21) Appl. No.: 17/776,379

(22) PCT Filed: Nov. 12, 2020

(86) PCT No.: PCT/EP2020/081961
§ 371 (c)(1),
(2) Date: May 12, 2022

(87) PCT Pub. No.: WO2021/094483
PCT Pub. Date: May 20, 2021

(65) Prior Publication Data
US 2022/0378997 A1    Dec. 1, 2022

(30) Foreign Application Priority Data
Nov. 15, 2019  (FR) ..................... 1912763

(51) Int. Cl.
*A61M 1/02*    (2006.01)
*A61M 1/36*    (2006.01)
(Continued)

(52) U.S. Cl.
CPC ........ *A61M 1/3636* (2014.02); *A61M 1/0218* (2014.02); *A61M 1/0281* (2013.01);
(Continued)

(58) Field of Classification Search
CPC .............. A61M 1/3636; A61M 1/0218; A61M 1/0281; A61M 2202/0439; B01D 39/163; B01D 39/18; B01D 2239/10
See application file for complete search history.

(56) References Cited

U.S. PATENT DOCUMENTS 3,965,906 A * 6/1976 Karami ............. A61F 13/15674
                                                  604/383
4,923,620 A   5/1990 Pall

FOREIGN PATENT DOCUMENTS

EP    0080383 B1 *  2/1987 ......... D04H 1/43838
EP    1336417 A1    8/2003
(Continued)

OTHER PUBLICATIONS

Machine translation of WO 2015197955.*
(Continued)

*Primary Examiner* — Benjamin L Lebron
(74) *Attorney, Agent, or Firm* — Harris Beach Murtha Cullina, PLLC

(57) ABSTRACT

The invention relates to a filtration unit for the leucocytapheresis of the blood or of a blood product. The filtration unit has an external pouch with at least one inlet orifice and with at least one outlet orifice. the external pouch contains a porous element interposed between the orifices. The porous element has at least one leucocytapheresis medium that works by adsorbing and/or by filtering out the leucocytes, and at least one nonwoven layer provided with bumps, each of the bumps having a perforation passing through it in the heightwise direction.

17 Claims, 4 Drawing Sheets

(51) Int. Cl.
  *B01D 39/16*    (2006.01)
  *B01D 39/18*    (2006.01)
(52) U.S. Cl.
  CPC ........... *B01D 39/163* (2013.01); *B01D 39/18* (2013.01); *A61M 2202/0439* (2013.01); *B01D 2239/10* (2013.01)

(56) References Cited

FOREIGN PATENT DOCUMENTS

| | | |
|---|---|---|
| EP | 2286821 A1 | 2/2011 |
| EP | 2671600 A1 | 4/2013 |
| GB | 2208666 A | 4/1989 |
| WO | 2004022831 A1 | 3/2004 |
| WO | 2013110694 A1 | 8/2013 |
| WO | 2015197955 A1 | 12/2015 |

OTHER PUBLICATIONS

Written opinion of the international searching authority, PCT/EP2020/081961. Jan. 22, 2021.*

International Search Report issued in corresponding application No. PCT/EP2020/081961 dated Jan. 22, 2021.

* cited by examiner

[Fig. 1]
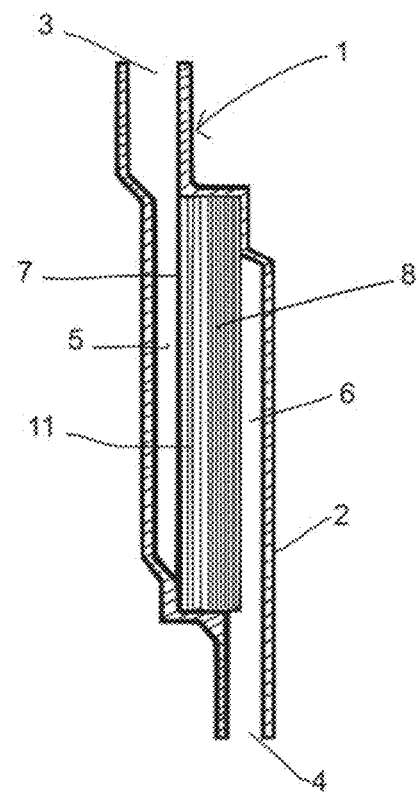
[Fig. 2]
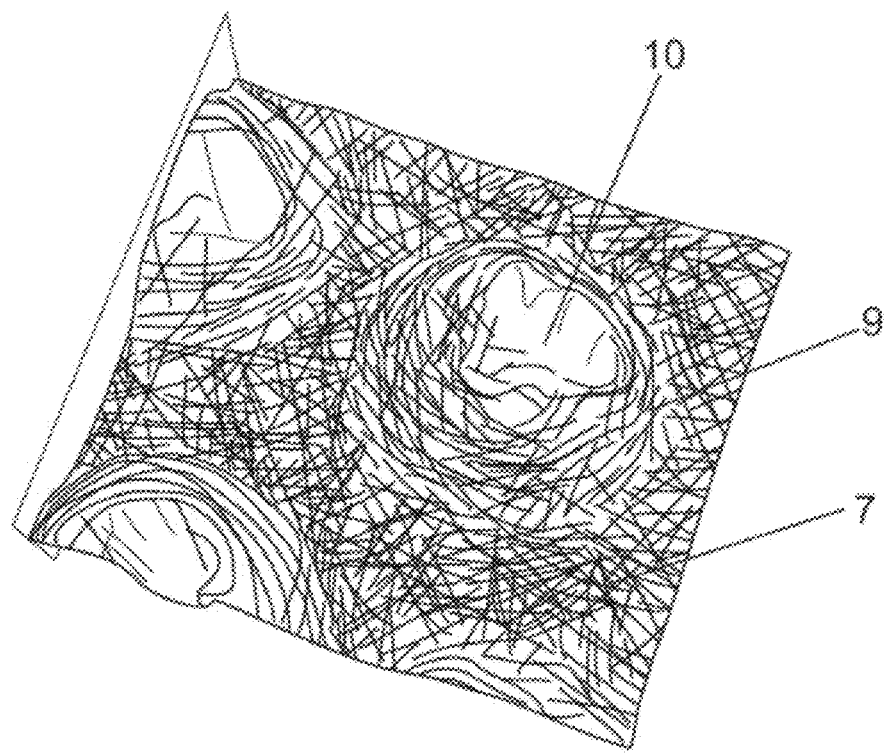

[Fig. 3]
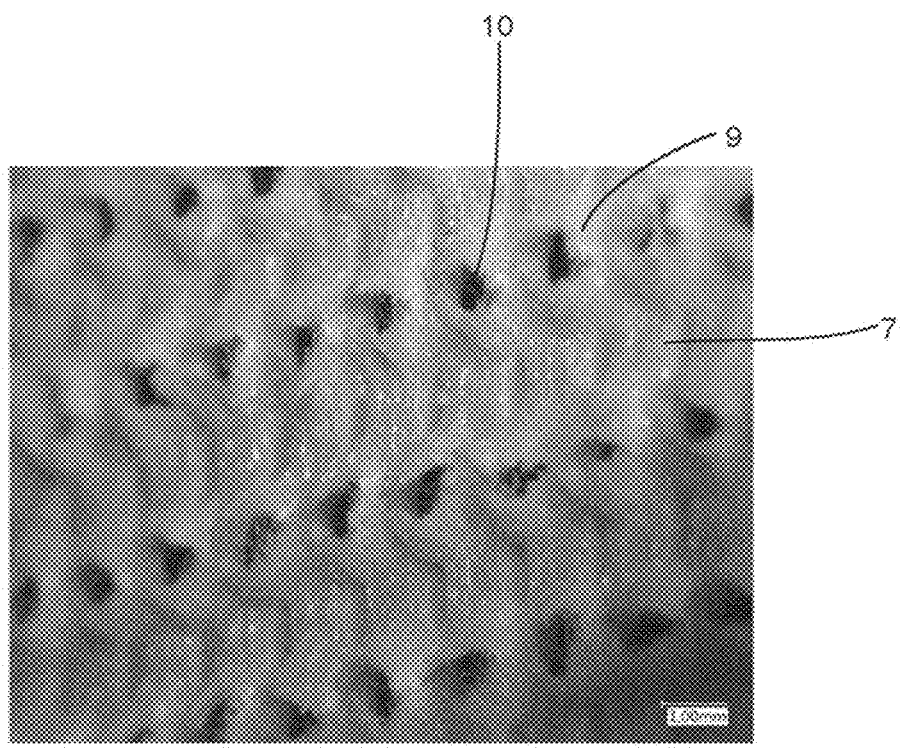
[Fig. 4]
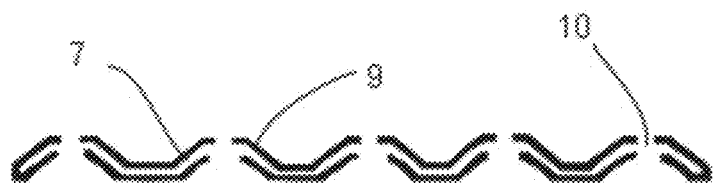

[Fig. 5]
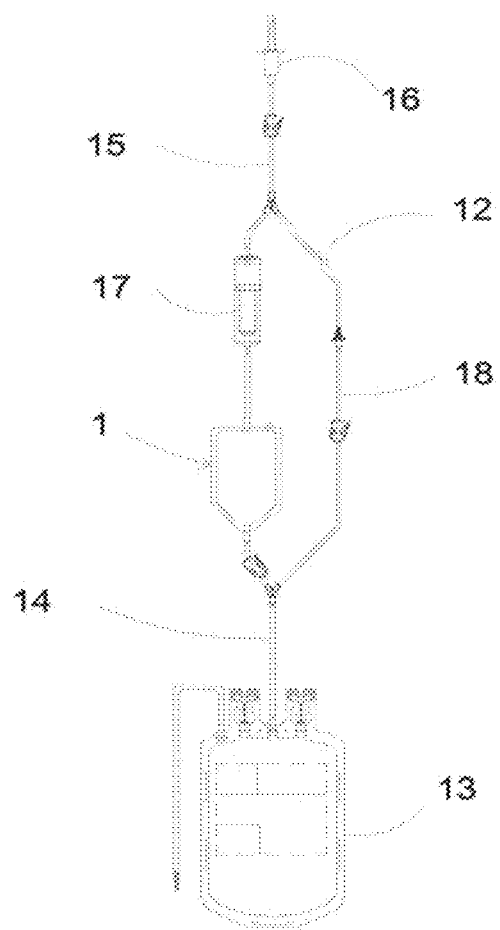
[Fig. 6]
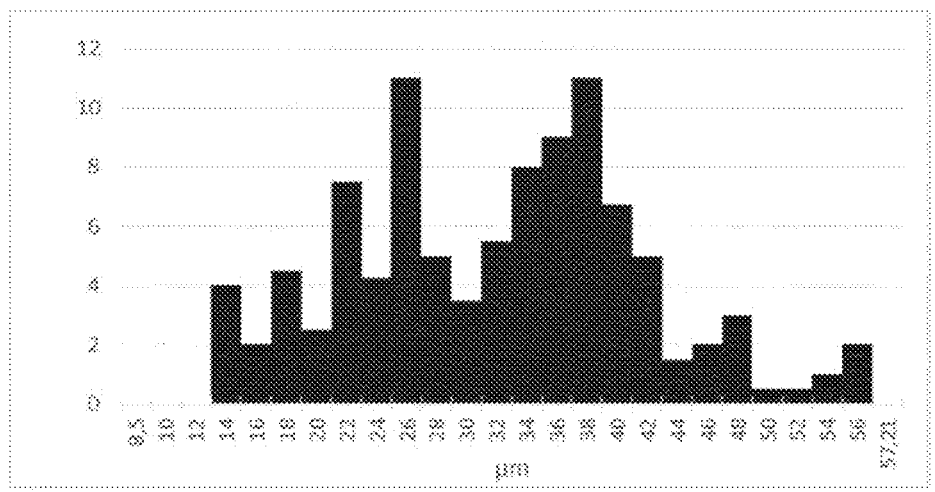

[Fig. 7]
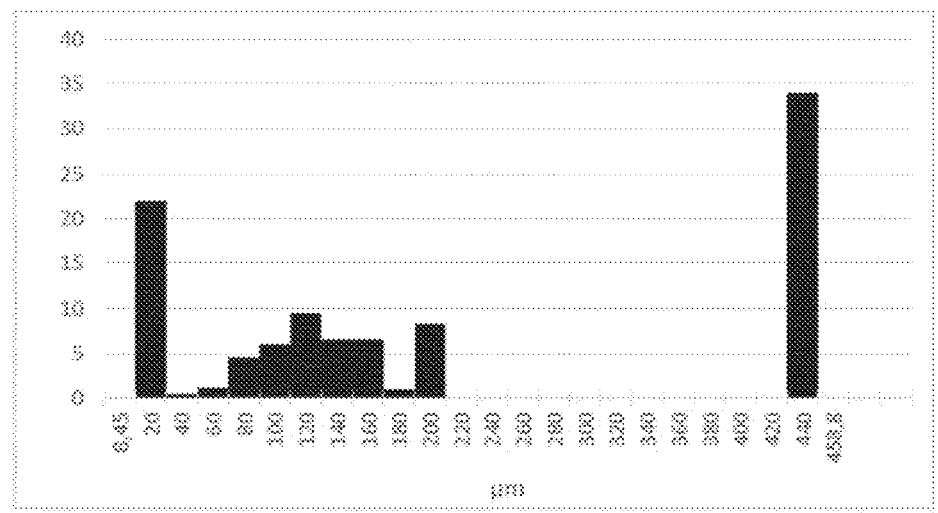
[Fig. 8]
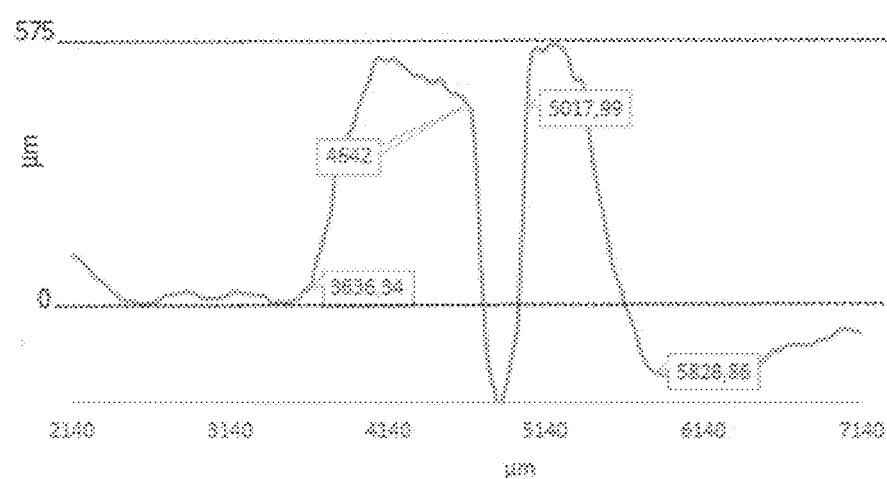

FILTRATION UNIT FOR THE LEUCOCYTAPHERESIS OF THE BLOOD, COMPRISING A RELIEF-PERFORATED NONWOVEN

CROSS REFERENCE TO RELATED APPLICATIONS

The instant application is a U.S. National Stage application of and claims priority to PCT/EP2020/081961, filed on Nov. 12, 2020, which is a PCT application of and claims priority to FR Application No. FR 1912763, filed on Nov. 15, 2019, the subject matter of both aforementioned applications are hereby incorporated by reference in their entireties.

TECHNICAL FIELD

The invention relates to a filtration unit for removing leucocytes from the blood or a blood product, a method for manufacturing said filtration unit comprising a layer of relief-perforated nonwoven, an extracorporeal leucodepletion method using such a unit and a bag system comprising such a unit.

BACKGROUND

The invention typically applies to the filtration of the blood or a blood product, and more particularly to the removal of leucocytes from whole blood or from a concentrate of red blood cells.

The blood or a blood product, after its collection and separation in the case of a product, is intended in particular to be transfused to a patient having need of it. It is well-known that leucocytes are undesirable during this transfusion in that they are likely to cause harmful and/or potentially dangerous reactions in the patient. Indeed, the leucocytes increase the risk of immune rejection such as graft-versus-host disease and promote the transmission of infectious agents.

This is why it is recommended, or even imposed in certain countries, to perform a leucodepletion on the blood or the blood product before its transfusion, and to do so with a given yield.

To date, the optimum solution for removing the leucocytes is to filter the blood or the blood product through a filtration unit provided with a leucodepletion medium.

Such a leucodepletion medium comprises one or more layers produced from a polymer material and chosen so as to improve the rate of leucodepletion, the recovery of blood products, the filtration time and/or the selectivity of the filtration.

The majority of leucodepletion media comprise layers of nonwovens. A nonwoven is defined as a manufactured sheet, formed from a web or a ply of directionally or randomly orientated fibres, bonded by friction and/or cohesion and/or adhesion, with the exclusion of paper and products obtained by weaving, knitting, tufting, seams incorporating binding threads or filaments or felted by wet fulling, whether or not they are needled.

These nonwovens are produced by melting or by direct spinning. The spun-bond nonwoven makes it possible to obtain fibres having a diameter generally less than 20 μm. In the case of melt-blown fibres obtained by a blown extrusion technique, the fibres generally have a diameter less than 5 μm. The spun-bond or melt-blown nonwovens therefore have a relatively dense structure capable of retaining the leucocytes by a mechanism for adsorbing and/or filtering out at the surface (or sieving).

In addition to a leucodepletion medium, the filtration units also generally comprise a pre-filter for eliminating micro-aggregates. For example, in document EP 1 336 417, a layer of polyester having a permeability between 1000 and 5000 L/m²/s and a pore size of approximately 35 μm is disposed upstream of the leucodepletion medium.

Depending on the countries and the practices of blood banks, the blood products can be stored before filtration, for up to 14 days at 4° C. or at ambient temperature, with or without an additive solution such as, for example, saline-adenine-glucose-mannitol (SAGM) solution.

Under these conditions, the filtration times with filtration units of the type described in document EP 1 336 417 can increase up to a duration that may exceed one hour. These filtration units can also clog, so that the filtration stops and the blood product is lost.

This clogging and prolonged filtration times are essentially due to the presence of aggregates formed, in particular, of red blood cells, platelets and fibrin gel. The size of these aggregates increases with the duration of storage, able to range from 20 μm to 200 μm.

In order to remove these aggregates and retain the leucocytes, document U.S. Pat. No. 4,923,620 proposes a filtration unit comprising three elements: a needled web with a fibre diameter between 20 and 30 μm in order to remove the gels and aggregates, two or more intermediate layers of melt-blown nonwoven fibres to remove the micro-aggregates, and a plurality of final layers of melt-blown nonwoven fibres to remove the leucocytes, these fibres having a smaller diameter than that of the fibres of the intermediate layers. The needled web comprises an acrylic binder and is hot compressed in order to reduce its pore size to approximately 50 μm.

Document EP 2 286 821 describes a filter material for removing the aggregates comprising, on the one hand, short fibres having a titre between 0.7 and 4 decitex (dtex) and a length between 1 and 80 mm and, on the other hand, a base fabric comprising long spun-bond fibres. The short fibres have a three-dimensional structure and are entangled, in particular by water jet, in the long fibres, so as to obtain a mass per unit area between 10 and 80 g/m².

Document WO2013/110694 proposes using fibres having a groove, in particular trilobal fibres from spun-bond or melt-blown technology, in order to remove, from the blood products, aggregates, gels, cellular debris and other fragments.

Finally, document WO2015/197955 discloses a pre-filter material for filtering out leucocytes from the blood, comprising a heat-bonded carded web formed of at least two types of discontinuous fibres. This web has a structure that is sufficiently permeable to retain the aggregates without risk of clogging, while having a sufficient mechanical strength to be incorporated in a filtration unit.

In addition, in the field of hygiene products, in particular feminine hygiene products, it is known to use a perforated nonwoven material such as that described in document GB 2 208 666, improving the transfer of liquids to absorbent materials placed downstream of the perforated nonwoven.

The applicant has identified that this type of perforated nonwoven material could be advantageously used in blood filtration units in order to retain the aggregates and other gels of the blood while significantly reducing the risk of clogging.

To this effect and according to a first aspect, the invention proposes a filtration unit intended to allow the leucodepletion of the blood or of a blood product, comprising an external pouch provided with at least one inlet orifice and with at least one outlet orifice, the pouch containing a porous element interposed between said orifices, said porous element comprising at least one leucodepletion medium that works by adsorbing and/or by filtering out the leucocytes, and at least one layer of nonwoven provided with a plurality of bumps, each of said bumps having a perforation passing through it in the heightwise direction to form a relief-perforated nonwoven layer.

According to another aspect, the invention relates to a method for manufacturing a filtration unit according to the first aspect of the invention, comprising:

forming a layer of perforated nonwoven by embossing and piercing a layer of nonwoven between two rollers, at least one of which is provided with a plurality of needles, so as to perforate the nonwoven while creating bumps around the perforations which are elevated relative to the surface of the nonwoven;

assembling said layer of relief-perforated nonwoven with a leucodepletion medium so as to form a porous element, and disposing said porous element in an external pouch of a filtration unit.

The invention also relates to an extracorporeal method for leucodepletion of the blood or a blood product comprising the passing of said blood or said blood product contained in a bag through a filtration unit according to the first aspect of the invention.

According to yet another aspect, the invention relates to a system of bags for leucodepletion of the blood or a blood product comprising a bag for collecting the filtrate connected, by means of a tube and at an inlet orifice, to an outlet orifice of a filtration unit according to the first aspect.

BRIEF DESCRIPTION OF THE DRAWINGS

Other objects and advantages will appear in the course of the description which follows.

FIG. 1 shows a schematic view of a filtration unit according to the invention.

FIG. 2 shows a drawing of the microscope surface of a relief-perforated spun-bond nonwoven layer.

FIG. 3 shows a scanning electron microscope photograph of a relief-perforated melt-blown fibre nonwoven layer.

FIG. 4 shows a schematic view in section and profile of a slice of relief-perforated nonwoven.

FIG. 5 shows a schematic view of a bag system comprising a filtration unit according to the invention.

FIG. 6 shows the distribution of pores sizes of a nonwoven before perforation.

FIG. 7 shows the distribution of pores sizes of the nonwoven of FIG. 6 after perforation.

FIG. 8 shows the optical measurement of a bump of a relief-perforated nonwoven.

The filtration unit according to the invention is intended to allow leucodepletion of the blood or a blood product.

DETAILED DESCRIPTION

Blood product shall mean, in particular, red blood cell concentrates, platelet concentrates, plasma, platelet-poor or platelet-rich plasma and the leucocyte and platelet layer or buffy coat. Red blood cell concentrates are generally obtained by gentle centrifugation of a unit of whole blood and then extraction of the layer of platelet-rich plasma. In an alternative, red blood cell concentrates are obtained by hard centrifugation of a unit of whole blood and then extraction of the layer of platelet-poor plasma. The red blood cell concentrates are then termed "not depleted of leucocytes and platelets". In another alternative, the red blood cell concentrates are obtained by hard centrifugation of a unit of whole blood and then extraction of the buffy layer and the platelet-poor plasma layer. The red blood cell concentrates are then termed "depleted of leucocytes and platelets".

Referring to FIG. 1, the filtration unit 1 comprises an external pouch 2 provided with at least one inlet orifice 3 and at least one outlet orifice 4, the pouch 2 containing a porous element interposed between said orifices 3, 4. The porous element forms, with the pouch 2, an inlet compartment 5 intended to collect the fluid to be filtered, said inlet compartment 5 communicating with the inlet orifice 3, and an outlet compartment 6 intended to collect the filtrate, said outlet compartment 6 communicating with the outlet orifice 4.

The external pouch 2 of the filtration unit is flexible, rigid or semi-rigid. For example, the pouch is made of polycarbonate, polyvinyl chloride or a polyolefin, such as polypropylene, polyethylene or a polypropylene-based complex.

The direction of flow of the fluid in the filtration unit, from the inlet 3 to the outlet 4, makes it possible to define the terms "upstream" and "downstream" used in the description.

The porous element includes at least one leucodepletion medium 8 that works by adsorbing and/or by filtering out the leucocytes.

According to the invention, the porous element further encloses at least one layer of nonwoven 7 provided with a plurality of bumps 9, each of said bumps having a perforation 10 passing through it in the heightwise direction so as to form a relief-perforated nonwoven layer. Such a layer is illustrated in FIGS. 2 to 4.

The nonwoven consists of fibres that are tangled together but which are not woven or knitted. The nonwoven is, for example, a nonwoven of melt-blown fibres or a spun-bond nonwoven.

The relief-perforated nonwoven comprises thermoplastic fibres of a biocompatible polymer such as polyester, polypropylene, polyethylene, polyamide, cellulose or the mixtures of these polymers. In particular, the fibres are polyester fibres, in particular polyethylene terephthalate.

The perforated bumps are produced by embossing and piercing the nonwoven all the way through. For example, the layer of relief-perforated nonwoven is manufactured by embossing and piercing a layer of nonwoven between two rollers, at least one of which is provided with a plurality of needles. In this way, the nonwoven is perforated while creating bumps 9 around the perforations 10 which are elevated with respect to the surface of the nonwoven. These bumps 9 are hollow and delimit the perforations. In particular, the bumps 9 have substantially all the same dimensions and are formed on the same side of the nonwoven.

Advantageously, the relief-perforated nonwoven is a spun-bond nonwoven which has advantageous mechanical properties, in particular in terms of tensile strength. With this type of spun-bond nonwoven material, it is possible to form bumps 9 by embossing which are higher and more stable than with a melt-blown fibre nonwoven.

In particular, the bumps 9 are frustoconical in shape. The bumps 9 rise tapering from a surface of the nonwoven. Other three-dimensional shapes are possible.

The shape of the perforations substantially corresponds to the shape of the bumps. For example, in the case of a frustoconical bump, the perforation is frustoconical and the proximal and distal openings of the perforation are substantially circular or elliptical. The terms "proximal" and "distal" mean relative to the surface of the nonwoven.

The bumps 9 are separated from one another. They are distributed over the nonwoven in a regular or irregular manner. In particular, the bumps 9 form a distinct and repeated pattern on the nonwoven.

FIGS. 2 and 3 show an image, taken by a scanning electron microscope, of a relief-perforated nonwoven, of the spun-bond and melt-blown fibre type, respectively.

Unexpectedly, this layer of relief-perforated nonwoven has a good capacity to retain the aggregates and other gels present in the blood or in the blood product to be filtered, while avoiding its clogging. In addition, it is observed that the filtration times are reduced. The aggregates form during the storage of the blood and are substantially composed of red blood cells, platelets and fibrin gel.

Indeed, as schematically illustrated in FIG. 4, the presence of relief-perforated bumps 9 in the nonwoven 7 makes it possible to obtain a much thicker structure than the same non-perforated nonwoven, composed of peaks and troughs in which the aggregates can lodge without blocking the entire filtration surface of the nonwoven.

Advantageously, the layer of relief-perforated nonwoven is disposed in the filtration unit upstream of the leucodepletion medium in order to retain the aggregates of the blood or of the blood product before the leucodepletion.

More particularly, a plurality of layers of relief-perforated nonwoven, for example two or three layers, are disposed upstream of the leucodepletion medium.

Yet more particularly, the layer or layers of relief-perforated nonwoven are disposed in the furthest upstream part of the porous element of the filtration unit.

The relief-perforated nonwoven is asymmetric. In the filtration unit, the layer of relief-perforated nonwoven is disposed with the bumps 9 directed in the upstream direction or in the downstream direction of the filtration unit. In the case where the filtration unit comprises a plurality of relief-perforated nonwoven layers, the layers of relief-perforated nonwoven are disposed with the bumps 9 directed in the same direction or otherwise.

When the bumps 9 are directed in the downstream direction, the flow of blood or of the blood product in the filtration unit is facilitated while avoiding backflow.

According to an embodiment, the thickness of the layer of relief-perforated nonwoven is between 400 and 1 500 µm, measured with the help of a micrometer with a pressure of 10 kPa (standard ISO 9073-2:1995). A thickness in the range from 500 to 1300 µm is advantageous in order to obtain a thickness that is sufficient for trapping the aggregates.

The relief-perforated nonwoven has a mass per unit area in the range from 40 to 90 g/m$^2$, in particular in the range from 50 to 80 g/m$^2$.

Below 50 g/m$^2$, it would appear that the rate of leucodepletion degrades considerably, due to the too low density of fibres. Above 90 g/m$^2$, the fibre density is too high and the risk of blocking increases.

The air permeability of the layer of relief-perforated nonwoven is in the range from 800 to 3000 L/m$^2$/s.

The air permeability is determined according to standard NF EN ISO 9237 on a sample of at least 100 cm$^2$ using an air permeability meter such as the FX 3300 from TextTest with an air pressure regulated at 196 Pa (Standard EDANA 140.1).

An air permeability greater than 3000 L/m$^2$/s leads to a shorter filtration time, since the blood has potentially more space in which to circulate, but risks increasing the number of residual leucocytes. Below 800 L/m$^2$/s, the filtration time increases, as does the risk of blocking.

An air permeability of the layer of relief-perforated nonwoven in the range from 1300 to 2500 L/m$^2$/s is a good compromise between the filtration time, the occurrence of blockages and the leucodepletion rate.

The air permeability of the nonwoven layer depends on a plurality of parameters including the air permeability of the basic non-perforated nonwoven, the dimensions of the perforations and the number of perforations in the nonwoven.

In the case of a spun-bond nonwoven, the average diameter of the fibres is in the range from 5 µm to 30 µm, in particular from 8 µm to 20 µm.

The dimensions of the bumps 9 and of the perforations are determined by optical measurement and porometry.

The bumps 9 extend from the surface of the nonwoven to a height between 200 µm and 1 500 µm, in particular between 400 µm and 700 µm.

According to an embodiment, the bumps 9 have a distal opening, substantially cylindrical in shape, of diameter between 100 µm and 800 µm, in particular between 100 µm and 500 µm. The proximal opening of the bumps 9 is substantially cylindrical in shape, of diameter between 1000 µm and 3000 µm, in particular between 1500 µm and 2500 µm.

In particular, the relief-perforated nonwoven has a perforation rate in the range from 5 to 20 perforations per cm$^2$.

In addition to layer or layers of relief-perforated nonwoven, the porous element of the filtration unit comprises a leucodepletion medium 8 that works by adsorbing and/or by filtering out the leucocytes. This leucodepletion medium 8 comprises, in particular, one or more layers 11 of a nonwoven material of melt-blown fibres.

For example, the fibres of the leucodepletion medium 8 are chosen among fibres of polyethylene, polypropylene, polyethylene terephthalate, polybutylene terephthalate and the copolymers thereof.

Each layer 11 of the leucodepletion medium has an air permeability less than that of the relief-perforated nonwoven 7, so as to create an air permeability gradient decreasing from upstream to downstream.

In order to best retain the leucocytes, each layer 11 of the leucodepletion medium 8 has a permeability in the range from 90 to 500 L/m$^2$/s.

The mass per unit area of each layer 11 of the leucodepletion medium 8 is in the range from 20 to 80 g/m$^2$, in particular in the range from 30 to 60 g/m$^2$ for a thickness between 100 and 400 µm.

A method for manufacturing a relief-perforated nonwoven layer for filtering blood or a blood product with a filtration unit as described above, comprises embossing and piercing a layer of nonwoven between two rollers, at least one of which is provided with a plurality of needles, so as to perforate the nonwoven while creating bumps 9 around the perforations which are elevated relative to the surface of the nonwoven.

In order to facilitate and consolidate the creation of the perforated bumps 9 on the nonwoven, one of the rollers comprises a plurality of needles and the other roller comprises cavities, the geometry of which is suitable for the interlocking of said needles during the embossing. In addition, it is advantageous that at least one of the rollers is heated.

The layer of relief-perforated nonwoven thus obtained by this manufacturing method is used to remove the aggregates of the blood or a blood product intended to be filtered.

In particular, this layer of relief-perforated nonwoven is assembled with a leucodepletion medium in order to form a porous element, said porous element then being disposed in an external pouch of a filtration unit.

A method for manufacturing a filtration unit 1 according to the first aspect thus comprises:
- forming a layer of relief-perforated nonwoven by embossing and piercing a layer of nonwoven between two rollers, at least one of which is provided with a plurality of needles, so as to perforate the nonwoven while creating bumps 9 around the perforations 10 which are elevated relative to the surface of the nonwoven;
- assembling said layer of relief-perforated nonwoven with a leucodepletion medium so as to form a porous element, and
- disposing said porous element in an external pouch of a filtration unit.

The invention also relates to a method for leucodepletion of the blood or a blood product comprising the passage of said blood or said blood product through a filtration unit as described above.

In particular, the leucodepletion method is an extracorporeal method carried out outside of the human body, once the blood or the blood product is extracted and isolated from the donor. In particular, the blood or the blood product to undergo leucodepletion is contained in a bag.

According to another aspect and with reference to FIG. 5, the invention further relates to a system of bags 12 for leucodepletion of a fluid such as the blood or a blood product, comprising a bag 13 for collecting the filtrate, said bag 13 being connected, by means of a tube 14 and at an inlet orifice, to an outlet orifice of a filtration unit 1 according to the first aspect of the invention.

The system 12 further comprises connection means with a bag (not shown) containing the fluid to be filtered, which are connected, via a tube 15, to an inlet orifice of the filtration unit. The connection means are, for example, a perforator 16.

Alternatively, a bag (not shown) intended to contain the fluid to be filtered is pre-connected to the filtration unit 1 via the tube 15.

Hence, the fluid, once collected and transferred into a bag, can be introduced into the bag system 12 in order to be filtered by means of the filtration unit, the filtrate then being collected in the filtrate collection bag 13.

A drip chamber 17 is connected to the system on the tube 15 connecting the filtration unit 1 and the connection means to a bag containing the fluid to be filtered.

A branch tube 18 is connected on one hand to the tube 14 that connects the filtration unit 1 and the filtrate collecting bag 13, and on the other hand to the tube 15 connecting the filtration unit and the means for connecting to a bag containing the fluid to be filtered, upstream of the drip chamber 17, as necessary.

This branch tube 18 is used in order to flush the air from the bag 13 for collecting the filtrate and in order to purge the filtration unit 1.

Other well-known bag systems, such as those described in document EP 1 336 417 can be used in the context of the invention.

EXAMPLES

Example 1: Characterisation of Relief-Perforated Nonwovens

A spun-bond nonwoven was produced

The physical properties of a spun-bond nonwoven (SB) and a melt-blown fibre nonwoven (MB) before and after perforation are indicated below:

TABLE 1

|  | Thickness (μm) | Air permeability (L/m²/s at 196 Pa) |
|---|---|---|
| SB non-perforated | 330 | >800 |
| SB7 (7 perforations/cm²) | 680 | 2350-2370 |
| SB11 (11 perforations/cm²) | 670 | 2450-2490 |
| 2SB11 2 layers of PET11 | 1200 | 1480-1540 |
| MB not perforated | 430 | >300 |
| MB7 (7 perforations/cm²) | 430 | 1250-1480 |
| 2MB7 2 layers of MB7 | 800 | 590-650 |
| MB11 (11 perforations/cm²) | 540 | 1320-1810 |
| 2MB11 2 layers of MB11 | 990 | 800-920 |

The relief perforations have been characterised using a liquid extrusion porometer from PMI society.

The analytical results are as follows:

TABLE 2

| Pores | SB | SB11 | MB11 |
|---|---|---|---|
| Average (μm) | 34 | 161 | 15 |
| Minimum diameter (μm) | 8.5 | 8.4 | 3.7 |
| Maximum diameter (μm) | 57 | 459 | 208 |
| Mode | 38-40 μm | 440-450 μm | 10-20 μm |

FIG. 6 shows the size distribution of pores of the nonwoven SB before perforation and FIG. 7 the size distribution of the pores of the nonwoven SB11.

FIG. 8 shows the optical characterisation of the SB11. According to this optical characterisation, the height of a bump 9 is approximately 575 μm, the diameter of the distal opening of the perforation is approximately 375 μm and the diameter of the proximal opening of the perforation approximately 2200 μm.

Example 2: Filtration of a Red Blood Cell Concentrate Kept Cold for 7 Days

A first series of tests was carried out in order to test the performances of a filtration unit according to the invention with one or two layers of relief-perforated nonwoven.

The blood product to undergo leucodepletion is a concentrate of red blood cells obtained by gentle centrifugation (2000 g) of a sample of whole blood (450-480 ml) to which an anticoagulant (CPD) is added. In order to promote the formation of aggregates, the concentrate of red blood cells is kept without the addition of additive solution, for 7 days at 4° C. before filtration. The filtration is carried out at ambient temperature, the concentrate of red blood cells having a temperature of approximately 12-15° C.

Reference Filtration Unit 1

A filtration unit has been produced comprising, in a rigid casing, a porous element formed from upstream to downstream and stacked one on top of the other:
- a carded web consolidated by air crossing therethrough, comprising a mixture of PET fibres and Co-PET fibres having a permeability between 4000 and 5000 L/m²/s, a mass per unit area between 50 and 70 g/m², and a mean pore size of approximately 100 µm, two layers of melt-blown nonwoven made of polypropylene having a thickness of order 285 µm, and an air permeability of approximately 800 L/m²/s, as pre-filter layers, sixteen layers of melt-blown polypropylene nonwoven, each having a mass per unit area of approximately 40 g/m² and an air permeability of approximately 110 L/m²/s, as leucodepletion medium.

Filtration Unit 1

In the filtration unit, the carded web of the reference filtration unit has been replaced by a layer of relief-perforated nonwoven SB11, with the bumps 9 directed in the downstream direction of the filtration unit.

Filtration Unit 2

In the filtration unit 2, the carded web of the reference filtration unit has been replaced by two layers of perforated nonwoven SB11, stacked one on top of the other, with the bumps 9 directed in the downstream direction of the filtration unit.

Filtration Unit 3

In the Filtration Unit 3, the Carded Web of the Reference Filtration Unit has been replaced by two layers of perforated nonwoven SB11, with the bumps 9 directed in the upstream direction of the filtration unit.

Filtration Unit 4

In the filtration unit 4, the carded web of the reference filtration unit has been replaced by a layer of perforated nonwoven SB7. The bumps 9 are directed in the downstream direction of the filtration unit.

Filtration Unit 5

In the filtration unit 5, the carded web of the reference filtration unit has been replaced by two layers of melt-blown fibre nonwoven MB7, with the bumps 9 directed in the downstream direction of the filtration unit.

Filtration Unit 6

In the filtration unit 6, the carded web of the reference filtration unit has been replaced by a layer of nonwoven MB11, with the bumps 9 directed in the downstream direction.

Filtration Unit 7

In the filtration unit 7, the carded web of the reference filtration unit has been replaced by two layers of perforated nonwoven MB11, stacked one on top of the other, with the bumps 9 directed in the downstream direction of the filtration unit.

The leucodepletion results are shown in table 3.

TABLE 3

|  | Test number n= | Average filtration time +/− standard deviation (min) | Number of leucocytes (average)/bag | Loss (mL) | Average rate of leuco-depletion (log reduction) |
|---|---|---|---|---|---|
| Reference unit 1 | 10 | 51 +/− 28 | $2.15 \times 10^5$ | 20 | 4.47 |
| Filtration unit 1 | 11 | 49 +/− 20 | $6.56 \times 10^5$ | 19.5 | 4.05 |
| Filtration unit 2 | 10 | 43 +/− 17 | $2.2 \times 10^5$ | 19.2 | 4.25 |
| Filtration unit 3 | 11 | 53 +/− 30 | $4.07 \times 10^5$ | 19.2 | 4.17 |
| Filtration unit 4 | 11 | 35 +/− 19 | $3.83 \times 10^5$ | 18.7 | 4.16 |
| Filtration unit 5 | 3 | 75 +/− 33 | $4.53 \times 10^4$ | 21.4 | 4.96 |

TABLE 3-continued

|  | Test number n= | Average filtration time +/− standard deviation (min) | Number of leucocytes (average)/bag | Loss (mL) | Average rate of leuco-depletion (log reduction) |
|---|---|---|---|---|---|
| Filtration unit 6 | 3 | 210 +/− 150 | $1.93 \times 10^6$ | 26 | 3.63 |
| Filtration unit 7 | 5 | 104 +/− 94 | $6.21 \times 10^4$ | 23.8 | 4.37 |

It is noted that the filtration times of filtration units 5 to 7 comprising layers of perforated melt-blown nonwoven are longer than those of the other filtration units comprising layers of perforated spun-bond nonwoven. It is thus advantageous to use a layer of perforated spun-bond nonwoven in order to retain the aggregates.

Example 3: Filtration of a Red Blood Cell Concentrate that is not Depleted of Leucocytes and Platelets Another series of tests was carried out in order to test the performances of a filtration unit in a closed system according to the invention with one or two layers of relief-perforated nonwoven.

The blood product to undergo leucodepletion is a red blood cell concentrate that is not depleted of leucocytes and platelets, obtained by hard centrifugation of a sample of whole blood (450-480 ml) to which is added an anticoagulant (CPD) and kept at 4° C. for 3 days. The red blood cell concentrate is separated from the plasma, and the mixture of red blood cell concentrate and leucocyte and platelet layer is filtered at ambient temperature.

Reference Filtration Unit 2

A filtration unit has been produced comprising, in a flexible pouch, a porous element formed from upstream to downstream and stacked one on top of the other:

two layers of spun-bond nonwoven made of polyester having a thickness of approximately 330 µm, and an air permeability greater than 800 L/m²/s, 26 layers of melt-blown fibre nonwoven made of polypropylene forming a decreasing gradient of air permeability ranging from approximately 400 to approximately 70 L/m²/s, one layer of woven spun-bond nonwoven having a thickness of approximately 330 µm, and an air permeability greater than 800 L/m²/s.

Filtration Unit 8

In the filtration unit 8, the two first layers of spun-bond nonwoven of the reference filtration unit 2 have been replaced by two layers SB11 with the bumps 9 directed in the downstream direction of the filtration unit.

The leucodepletion results are shown in Table 4.

TABLE 4

|  | Test number n= | Average filtration time +/− standard deviation (min) | Loss (mL) | Blockage (%) | Recovery rate of red blood cells (%) |
|---|---|---|---|---|---|
| Reference unit 2 | 10 | — | — | 10 | 82 |
| Filtration unit 8 | 7 | 126 +/− 41 | 29.8 | 0 | 90 |

Example 4: Filtration of a Red Blood Cell Concentrate at Ambient Temperature

In this test, the blood product to undergo leucodepletion is a concentrate of red blood cells obtained by gentle centrifugation (2600 g) of a sample of whole blood (450-480 ml) to which an anticoagulant (CPD) is added. The red blood cell concentrate is separated from the platelet-rich plasma, mixed with an SAGM-type additive solution and filtered at ambient temperature. The filtration is carried out in the 8 hours following the sampling of blood, using the filtration unit 8.

The leucodepletion results are shown in Table 5.

TABLE 5

| | Test number n= | Average filtration time (min) | Loss (mL) | Blockage (%) | Recovery rate of red blood cells (%) | Number of white blood cells |
|---|---|---|---|---|---|---|
| Filtration unit 8 | 1 | 49 | 25 | 0 | 93 | $1.61 \times 10^5$ |

What is claimed is:

1. A filtration unit comprising an external pouch provided with at least one inlet orifice and with at least one outlet orifice, the external pouch containing a porous element interposed between the inlet and outlet orifices, the porous element comprising at least one leucodepletion medium and one layer of nonwoven provided with a plurality of bumps, each of the bumps having a perforation passing through it in the heightwise direction.

2. The filtration unit according to claim 1, wherein the bumps are frustoconical in shape.

3. The filtration unit according to claim 1, wherein the bumps form a distinct and repeated pattern on the nonwoven layer.

4. The filtration unit according to claim 1, wherein the layer of nonwoven is disposed upstream of the leucodepletion medium.

5. The filtration unit according to claim 1, wherein the nonwoven has a thickness in the range from 500 to 1300 μm.

6. The filtration unit according to claim 1, wherein the nonwoven has a mass per unit area in the range from 40 to 90 g/m².

7. The filtration unit according to claim 1, wherein the nonwoven has an air permeability in the range from 800 to 3000 L/m²/s.

8. The filtration unit according to claim 1, wherein the bumps extend from the surface of the nonwoven to a height between 200 μm and 1500 μm.

9. The filtration unit according to claim 1, wherein the nonwoven has a perforation rate in the range from 5 to 20 perforations per cm².

10. The filtration unit according to claim 1, wherein the nonwoven is a spun-bond nonwoven.

11. The filtration unit according to claim 1, wherein the leucodepletion medium comprises one or more layers of a melt-blown fibre nonwoven material.

12. The filtration unit according to claim 1, wherein the leucodepletion medium comprises one or more layers of a nonwoven material, each layer of the leucodepletion medium having a permeability in the range from 90 to 500 L/m²/s.

13. The filtration unit according to claim 1, wherein the leucodepletion medium comprises one or more layers of a nonwoven material, each layer of the leucodepletion medium having an air permeability less than that of the nonwoven layer.

14. A method for manufacturing a filtration unit according to claim 1, wherein the method comprises:
    forming a nonwoven layer by embossing and piercing a nonwoven material between two rollers, at least one of which is provided with a plurality of needles;
    perforating the nonwoven material with the needles and creating bumps around the perforations which are elevated relative to the surface of the nonwoven material;
    assembling the nonwoven layer with a leucodepletion medium to form a porous element, and
    disposing the porous element in an external pouch of the filtration unit.

15. The manufacturing method according to claim 14, wherein one of the rollers comprises a plurality of needles and the other roller comprises cavities, the geometry of which is suitable for the interlocking of the needles during the embossing.

16. An extracorporeal method for leucodepletion of the blood or a blood product comprising the passing of the blood or the blood product contained in a bag through a filtration unit according to claim 1.

17. A bag system for leucodepletion of the blood or a blood product, wherein the system comprises a bag for collecting a filtrate, the bag being connected, with a tube and at an inlet orifice, to an outlet orifice of a filtration unit according to claim 1.

* * * * *